(12) United States Patent
Ye et al.

(10) Patent No.: US 8,900,260 B2
(45) Date of Patent: Dec. 2, 2014

(54) SURGICAL MILLING CUTTER

(75) Inventors: Lei Ye, Chongqing (CN); Jian Zhou, Chongqing (CN); Hua Feng, Chongqing (CN); Fei Li, Chongqing (CN); Hengyang Zhu, Chongqing (CN); Congxiao Li, Chongqing (CN)

(73) Assignee: Chongqing Runze Pharmaceutical Co., Ltd, Chongqing (CN)

(*) Notice: Subject to any disclaimer, the term of this patent is extended or adjusted under 35 U.S.C. 154(b) by 107 days.

(21) Appl. No.: 13/822,937

(22) PCT Filed: Aug. 24, 2011

(86) PCT No.: PCT/CN2011/078817
§ 371 (c)(1),
(2), (4) Date: Mar. 13, 2013

(87) PCT Pub. No.: WO2012/041133
PCT Pub. Date: Apr. 5, 2012

(65) Prior Publication Data
US 2013/0184731 A1    Jul. 18, 2013

(30) Foreign Application Priority Data

Sep. 30, 2010   (CN) .......................... 2010 1 0298082

(51) Int. Cl.
| A61B 17/32 | (2006.01) |
| --- | --- |
| A61B 17/00 | (2006.01) |
| B23B 31/16 | (2006.01) |
| A61C 3/02 | (2006.01) |
| A61B 17/16 | (2006.01) |
| A61B 19/00 | (2006.01) |

(52) U.S. Cl.
CPC ............... *A61B 17/32* (2013.01); *A61B 17/162* (2013.01); *A61B 17/32002* (2013.01); *A61B 2019/481* (2013.01)
USPC ............... 606/170; 606/80; 279/75; 433/165

(58) Field of Classification Search
CPC ....................................................... A61B 17/32
USPC ................. 606/170, 132, 133, 137, 168, 169, 606/79–80; 600/564; 30/160–163; 279/75; 433/165
See application file for complete search history.

(56) References Cited

U.S. PATENT DOCUMENTS 5,505,737 A * 4/1996 Gosselin et al. ................. 606/79

FOREIGN PATENT DOCUMENTS

CN    201211208 Y  *  3/2009

* cited by examiner

*Primary Examiner* — Todd Manahan
*Assistant Examiner* — Erich Herbermann

(57) ABSTRACT

A surgical milling cutter includes a milling cutter bracket, a locking device and a bottom electric motor connected successively. The milling cutter bracket includes a fixing seat with a through hole. A finger guide apparatus with an L-type first bracket at the top end thereof is provided on the upper part of the fixing seat. The end of the L-type first bracket's short side is provided with a downward projection. The lowest point of the projection is lower than that of the milling cutter's cylindrical head when the milling cutter is working normally. The surgical milling cutter utilizes the projection to prevent the possibility of an object contacting with the cylindrical head, thus avoiding an object being cut unevenly. Meanwhile, the L-type bracket can be driven by the finger guide apparatus to rotate so as to change the running direction of the milling cutter, thus facilitating surgical procedures.

7 Claims, 3 Drawing Sheets

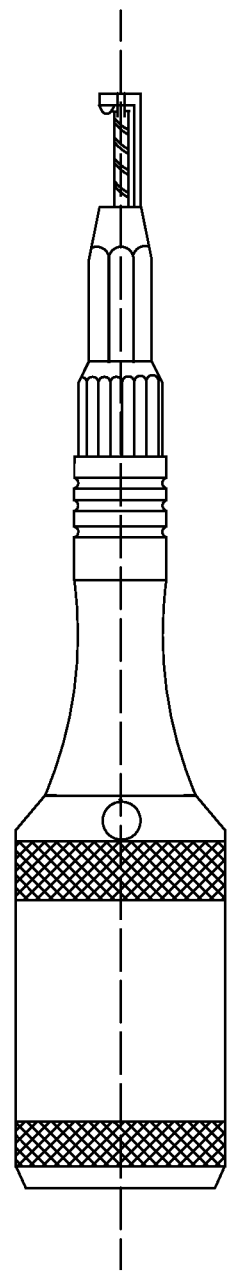
F I G. 1

SURGICAL MILLING CUTTER

BACKGROUND OF THE INVENTION

1. Field of the Invention

The present invention relates to a surgical cutting machine, and more particularly to a surgical milling cutter.

2. Description of the Prior Art

During a surgical operation, a milling cutter is used for cutting. The milling cutter comprises a milling cutter bracket, a blade and an electric motor. The top of the milling cutter bracket has an L-shaped support frame. The short side of the L-shaped support frame has a hole. The cylindrical head at the front part of the blade of the milling cutter extends into the hole to ensure that the milling cutter provides a better effect. In order to protect the milling cutter, the cylindrical head doesn't fully extend into the hole so a portion of the cylindrical head is exposed. In the existing technology, the short side of the L-shaped support frame is a flat configuration. When cutting an object, the cylindrical head doesn't work if it touches the object. The object will be cut unevenly. During cutting, it is difficult for the milling cutter to change direction so it is not convenient for use.

Accordingly, the inventor of the present invention has devoted himself based on his many years of practical experiences to solve these problems.

SUMMARY OF THE INVENTION

The primary object of the present invention is to provide a surgical milling cutter which can prevent a cylindrical head from contacting an object to be cut. The surgical milling cutter is nimble to change direction.

In order to achieve the aforesaid object, the surgical milling cutter comprises a milling cutter bracket, a locking device and a bottom electric motor connected successively. The milling cutter bracket comprises a fixing seat with a through hole. A finger guide apparatus with an L-type first bracket at the top end thereof is provided on the upper part of the fixing seat. The distal end of a short side of the L-type first bracket is provided with a downward projection. The lowest point of the projection is lower than that of a cylindrical head of the milling cutter when the milling cutter is working normally.

A T-shaped bolt having a through hole is fixed within the cavity of the finger guide apparatus. A first depressor is provided on the upper part of the fixing seat. A nut passes through a hole of the first depressor and is connected to the bolt.

The locking device comprises a protruding platform with a through hole and a bearing arranged on an inner wall of a small cylinder on the protruding platform. A locking sleeve is fitted on the protruding platform. The locking sleeve has a protrusion arranged on an upper part of an inner wall of the locking sleeve and a conical face arranged on a lower part of the inner wall of the locking sleeve. A spring is provided between a bottom of the conical face and an upper bottom face of the protruding platform. A second depressor is threadedly connected to an outer wall of the top part of the small cylinder on the protruding platform and presses the protrusion. A conical hole is arranged on a wall of the small cylinder on the protruding platform and communicates with the through hole of the protruding platform. A steel ball is arranged in the conical hole.

For the transmission rod to be applied with even force, the locking device comprises two bearings respectively located under the outer wall and above an upper bottom face.

For firmness of the two bearings, a support member is provided between the two bearings.

For convenient connection of a speed reducer, an inner wall of a big cylinder under the protruding platform has inner threads.

A bolt having a through hole is fixed within a cavity of the finger guide apparatus. A depressor is provided on the upper part of the fixing seat. A nut passes through a hole of the depressor and is connected to the bolt.

Alternatively, the lower part of the fixing seat is provided with a finger guide apparatus. A T-shaped bolt having a through hole is fixed within a cavity of the finger guide apparatus. A depressor is provided on the upper part of the fixing seat. A nut passes through a hole of the depressor and is connected to the bolt.

For keeping stable working of the milling cutter, the upper part of the finger guide apparatus is provided with a bearing.

To prevent the finger guide from being too nimble, a spring is fitted on the bolt.

For skidproof, the outer surfaces of the fixing seat and the finger guide apparatus each have a skidproof groove.

The protrusion of the present invention is able to prevent an object from contacting the cylindrical head, thus avoiding cutting the object unevenly. Additionally, by driving the L-shaped support frame to rotate via the finger guide apparatus, the movement direction of the milling cutter can be changed, facilitating the operation.

BRIEF DESCRIPTION OF THE DRAWINGS

FIG. 1 is a schematic view according to the preferred embodiment of the present invention;

DETAILED DESCRIPTION OF THE PREFERRED EMBODIMENTS

Embodiments of the present invention will now be described, by way of example only, with reference to the accompanying drawings.

Figure 2:
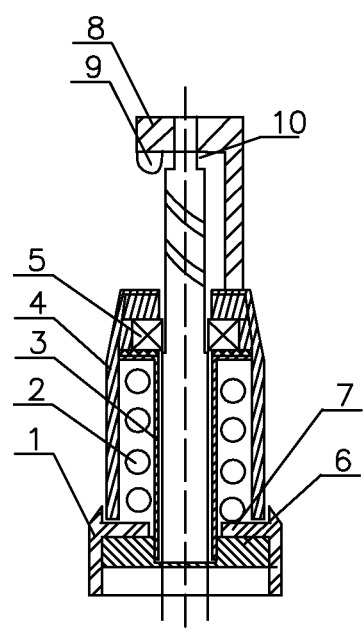
FIG. 2 is a sectional view showing the milling cutter bracket according to the preferred embodiment of the present invention.
Figure 3:
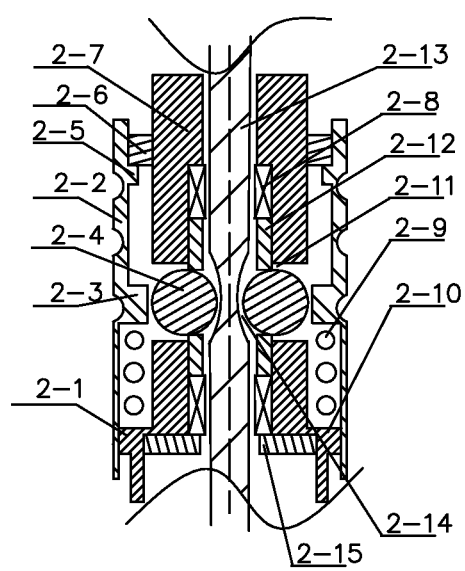
FIG. 3 is a sectional view showing the locking device according to the preferred embodiment of the present invention.

As shown in FIG. 1 to FIG. 3, a surgical milling cutter comprises a milling cutter bracket, a locking device and a bottom electric motor connected successively. The milling cutter bracket comprises a fixing seat (1) with a through hole. A finger guide apparatus (4) with an L-type first bracket at the top end thereof is provided on the upper part of the fixing seat (1). The distal end of a short side (8) of the L-type first bracket is provided with a downward projection (9). The lowest point of the projection (9) is lower than that of a cylindrical head (10) of the milling cutter when the milling cutter is working normally. The surgical milling cutter utilizes the projection (9) to prevent the possibility of an object contacting with the cylindrical head (10), thus avoiding the phenomenon of an object being cut unevenly. A T-shaped bolt (3) having a through hole is fixed within the cavity of the finger guide apparatus (4). A first depressor (7) is provided on the upper part of the fixing seat (1). A nut (6) passes through a hole of the first depressor (7) and is connected to the bolt (3).

The locking device comprises a protruding platform (2-1) with a through hole and a bearing (2-8) arranged on an inner wall of a small cylinder on the protruding platform (2-1). In this embodiment, the locking device comprises two bearings (2-8) respectively located under an outer wall (2-7) and above an upper bottom face (2-10). A support member (2-12) is provided between the two bearings (2-8). The two bearings (2-8) can effectively ensure stability of the transmission rod and decrease heat when rotating. The upper bottom face (2-10) is threadedly connected with the tightening member (2-15) to hold against the bearings (2-8) and the support member (2-12). The support member (2-12) is to enhance firmness of the bearings (2-8).

A locking sleeve (2-2) is fitted on the protruding platform (2-1). The locking sleeve (2-2) has a protrusion (2-5) arranged on an upper part of an inner wall of the locking sleeve (2-2) and a conical face (2-3) arranged on a lower part of the inner wall of the locking sleeve (2-2). A spring (2-9) is provided between a bottom of the conical face (2-3) and the upper bottom face (2-10) of the protruding platform (2-1). A second depressor (2-6) is threadedly connected to the outer wall (2-7) of the top part of the small cylinder on the protruding platform (2-1) and presses the protrusion (2-5). A conical hole (2-11) is arranged on the wall of the small cylinder on the protruding platform (2-1) and communicates with the through hole of the protruding platform (2-1). A steel ball (2-4) is arranged in the conical hole (2-11). The conical hole (2-11) corresponds in position to a recess (2-14) of the transmission rod (2-13) of the milling cuter. An inner wall of a big cylinder under the protruding platform (1) has inner threads. In this embodiment, the number of the conical holes (2-11) and the steel balls (2-4) is two as an equivalent change. The number can be three for a better locking effect.

When it is necessary to insert the transmission rod, the locking sleeve is pressed down. At this moment, the conical face is moved down and the steel ball rolls outward. After the transmission rod reaches a desired position, the locking sleeve is released. Through the spring, the locking sleeve ascends and the conical face holds against the steel ball to move inward to engage with the recess of the transmission rod in order to position the transmission rod. This locking way is easy and convenient to lock or unlock, lock firmly, and offer an improved safety.

The upper part of the finger guide apparatus (4) is provided with a bearing (5). A spring (2) is fitted on the bolt (3). The outer surfaces of the fixing (1) and the finger guide apparatus (4) each have a skidproof groove. The bearing (5) makes the milling cutter have a closer force point to ensure working of the milling cutter. The spring (2) is to ensure a certain force between the finger guide apparatus (4) and the fixing seat (1), preventing the finger guide apparatus (4) from turning too much to cause an operating error.

When the finger guide apparatus (4) is turned, the bolt (3) and the nut (6) are driven to turn. Thus, by driving the L-shaped support frame to rotate via the finger guide, the movement direction of the milling cutter can be changed, facilitating the operation.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A surgical milling cutter, comprising a milling cutter bracket, a locking device and a bottom electric motor connected successively, the milling cutter bracket comprising a fixing seat (1) with a through hole, a finger guide apparatus (4) with an L-type first bracket at the top end thereof being provided on an upper part of the fixing seat (1), a distal end of a short side (8) of the L-type first bracket being provided with a downward projection (9), a lowest point of the projection (9) being lower than that of a cylindrical head (10) of the milling cutter when the milling cutter is working;

a T-shaped bolt (3) having a through hole being fixed within a cavity of the finger guide apparatus (4), a first depressor (7) being provided on the upper part of the fixing seat (1), a nut (6) passing through a hole of the first depressor (7) and being connected to the bolt (3);

the locking device comprising a protruding platform (2-1) with a through hole and a bearing (2-8) arranged on an inner wall of a small cylinder on the protruding platform (2-1), a locking sleeve (2-2) being fitted on the protruding platform (2-1), the locking sleeve (2-2) having a protrusion (2-5) arranged on an upper part of an inner wall of the locking sleeve (2-2) and a conical face (2-3) arranged on a lower part of the inner wall of the locking sleeve (2-2), a spring (2-9) being provided between a bottom of the conical face (2-3) and an upper bottom face (2-10) of the protruding platform (2-1), a second depressor (2-6) being threadedly connected to an outer wall (2-7) of a top part of the small cylinder on the protruding platform (2-1) and pressing the protrusion (2-5), a conical hole (2-11) being arranged on a wall of the small cylinder on the protruding platform (2-1) and communicating with the through hole of the protruding platform (2-1), a steel ball (2-4) being arranged in the conical hole (2-11).

2. The surgical milling cutter as claimed in claim 1, wherein the locking device comprises two bearings (2-8) respectively located under the outer wall (2-7) and above the upper bottom face.

3. The surgical milling cutter as claimed in claim 2, wherein a support member (2-12) is provided between the two bearings (2-8).

4. The surgical milling cutter as claimed in one of claims 1 to 3, wherein an inner wall of a big cylinder under the protruding platform (2-1) has inner threads.

5. The surgical milling cutter as claimed in claim 4, wherein an upper part of the finger guide apparatus (4) is provided with a bearing (5).

6. The surgical milling cutter as claimed in claim 5, wherein a spring (2) is fitted on the bolt (3).

7. The surgical milling cutter as claimed in claim 6, wherein outer surfaces of the fixing seat (1) and the finger guide apparatus (4) each have a skidproof groove.

* * * * *